(12) United States Patent
Smith et al.

(10) Patent No.: US 8,216,780 B2
(45) Date of Patent: Jul. 10, 2012

(54) METHOD FOR ENHANCED SENSITIVITY IN BACTERIOPHAGE-BASED DIAGNOSTIC ASSAYS

(75) Inventors: Jonathan Drew Smith, Boulder, CO (US); Breanna Leigh Dreiling, Longmont, CO (US); Breanna Christine Smith, Lyons, CO (US); John H. Wheeler, Boulder, CO (US)

(73) Assignee: MicroPhage (TM) Incorporated, Longmont, CO (US)

( * ) Notice: Subject to any disclaimer, the term of this patent is extended or adjusted under 35 U.S.C. 154(b) by 205 days.

(21) Appl. No.: 12/476,796

(22) Filed: Jun. 2, 2009

(65) Prior Publication Data

US 2009/0286232 A1   Nov. 19, 2009

Related U.S. Application Data

(60) Continuation-in-part of application No. 12/346,656, filed on Dec. 30, 2008, now abandoned, which is a division of application No. 10/823,294, filed on Apr. 12, 2004, now abandoned.

(60) Provisional application No. 61/058,120, filed on Jun. 2, 2008, provisional application No. 60/544,437, filed on Feb. 13, 2004, provisional application No. 60/557,962, filed on Mar. 31, 2004.

(51) Int. Cl.
*C12Q 1/70* (2006.01)
*C12Q 1/02* (2006.01)

(52) U.S. Cl. .............................. 435/5; 435/29
(58) Field of Classification Search .................. None
See application file for complete search history.

(56) References Cited

U.S. PATENT DOCUMENTS

| | | |
|---|---|---|
| 4,104,126 A | 8/1978 | Young |
| 4,797,363 A | 1/1989 | Teodorescu et al. |
| 4,861,709 A | 8/1989 | Ulitzur et al. |
| 5,085,982 A | 2/1992 | Keith |
| 5,168,037 A | 12/1992 | Entis et al. |
| 5,476,768 A | 12/1995 | Pearson et al. |
| 5,498,525 A | 3/1996 | Rees et al. |
| 5,620,845 A * | 4/1997 | Gould et al. ............ 435/5 |
| 5,656,424 A | 8/1997 | Jurgensen et al. |
| 5,658,747 A | 8/1997 | Feldsine et al. |
| 5,679,510 A | 10/1997 | Ray et al. |
| 5,710,005 A | 1/1998 | Rittenburg |
| 5,723,330 A | 3/1998 | Rees et al. |
| 5,789,174 A | 8/1998 | Mouton et al. |
| 5,824,468 A | 10/1998 | Scherer et al. |
| 5,888,725 A | 3/1999 | Sanders et al. |
| 5,914,240 A | 6/1999 | Sanders et al. |
| 5,958,675 A | 9/1999 | Wicks et al. |
| 5,985,596 A | 11/1999 | Wilson et al. |
| 6,037,118 A | 3/2000 | Thomas et al. |
| 6,090,541 A | 7/2000 | Wicks et al. |
| 6,265,169 B1 | 7/2001 | Cortese et al. |
| 6,300,061 B1 | 10/2001 | Jacobs, Jr. et al. |
| 6,355,445 B2 | 3/2002 | Cherwonogrodzky et al. |
| 6,428,976 B1 | 8/2002 | Chang et al. |
| 6,436,652 B1 | 8/2002 | Cherwonogrodzky et al. |
| 6,436,661 B1 | 8/2002 | Adams et al. |
| 6,461,833 B1 | 10/2002 | Wilson et al. |
| 6,524,809 B1 | 2/2003 | Wilson et al. |
| 6,544,729 B2 | 4/2003 | Sayler et al. |
| 6,555,312 B1 | 4/2003 | Nakayama et al. |
| 6,660,437 B2 | 12/2003 | Friedrich et al. |
| 6,660,470 B1 | 12/2003 | Sanders et al. |
| 7,166,425 B2 | 1/2007 | Madonna et al. |
| 2002/0045195 A1 | 4/2002 | Hubscher et al. |
| 2002/0127547 A1 | 9/2002 | Miller |
| 2002/0192676 A1 | 12/2002 | Madonna et al. |
| 2003/0027241 A1 | 2/2003 | Sayler et al. |
| 2004/0121403 A1 | 6/2004 | Miller |
| 2004/0137430 A1 | 7/2004 | Anderson et al. |
| 2004/0224359 A1 | 11/2004 | Madonna et al. |
| 2005/0003346 A1 | 1/2005 | Voorhees et al. |

FOREIGN PATENT DOCUMENTS

| | | |
|---|---|---|
| DE | 4314998 | * 11/1994 |
| EP | 0168933 A2 | 1/1986 |
| EP | 0228975 | * 7/1987 |
| EP | 0439354 | 7/1991 |
| EP | 1300082 | 4/2003 |
| WO | WO-8504189 | 9/1985 |
| WO | WO-8804326 | 6/1988 |
| WO | WO-9202633 A1 | 2/1992 |
| WO | WO-9317129 | 9/1993 |
| WO | WO-9406931 | 3/1994 |

(Continued)

OTHER PUBLICATIONS

Chatterjee et al., FEMS Microbiology Letters, 2000, 188:47-53.*

(Continued)

*Primary Examiner* — Zachariah Lucas
*Assistant Examiner* — Nicole Kinsey White
(74) *Attorney, Agent, or Firm* — Patton Boggs LLP

(57) ABSTRACT

A method of determining the presence or absence of a target microorganism in a sample to be tested, the method comprising: (a) combining with the sample an amount of bacteriophage capable of attaching to the target microorganism to create a bacteriophage-exposed sample; (b) providing conditions to the bacteriophage-exposed sample sufficient to allow the bacteriophage to attach to the target microorganism while inhibiting phage replication in a potentially cross-reactive, non-target microorganism; and (c) assaying the bacteriophage-exposed sample to detect the presence or absence of a bacteriophage marker to determine the presence or absence of the target microorganism; wherein the amount of the bacteriophage is between 10% to 70% of the threshold number of bacteriophage that the assay can detect, or between $1 \times 10^6$ pfu/mL and $7 \times 10^6$ pfu/mL.

9 Claims, 1 Drawing Sheet

FOREIGN PATENT DOCUMENTS

| WO | WO 98/08944 | * | 3/1998 |
|---|---|---|---|
| WO | WO-9818962 | | 5/1998 |
| WO | WO-0010013 | | 2/2000 |
| WO | WO 01/25395 | * | 4/2001 |
| WO | WO-02061117 A1 | | 8/2002 |
| WO | WO-03087772 A2 | | 10/2003 |
| WO | WO-2006012371 | | 2/2006 |
| WO | WO-2006083292 | | 8/2006 |
| WO | WO-2006105504 | | 10/2006 |
| WO | WO-2008064241 A2 | | 5/2008 |

OTHER PUBLICATIONS

In the US Patent and Trademark Office, U.S. Appl. No. 10/249,452, Non-Final Office Action dated Feb. 23, 2005, 12 pages; and corresponding response dated Aug. 26, 2005, 17 pages.

In the US Patent and Trademark Office, U.S. Appl. No. 10/249,452, Non-Final Office Action dated Feb. 7, 2006, 9 pages; and corresponding response dated Aug. 7, 2006, 7 pages, and supplemental response dated Aug. 30, 2006, 6 pages.

In the US Patent and Trademark Office, U.S. Appl. No. 10/823,294, Final Office Action dated Dec. 3, 2007, 14 pages; and corresponding response and RCE dated Mar. 3, 2008, 14 pages.

In the US Patent and Trademark Office, U.S. Appl. No. 10/823,294, Non-Final Office Action dated Apr. 25, 2008, 11 pages; and corresponding response dated Aug. 25, 2008, 5 pages.

In the US Patent and Trademark Office, U.S. Appl. No. 10/823,294, Non-Final Office Action dated Jul. 23, 2007, 20 pages; and corresponding response dated Nov. 21, 2007, 24 pages.

In the US Patent and Trademark Office, U.S. Appl. No. 10/823,294, Non-Final Office Action dated Sep. 30, 2008, 8 pages; no response made.

Bordner et al.; "Microbiological Methods for Monitoring the Environment"; EPA Report No. EPA-600/8-78-017; US Environmental Protection Agency; Cincinnati, Ohio 45268; Dec. 1978.

Cardullo; "Nonradioactive Fluorescence Resonance Energy Transfer"; Nonradioactive Labeling and Detection of Biomolecules; C. Kessler, Ed.; Springer-Verlag, NY; 1992; pp. 414-423.

Cudjoe et al.; "Immunomagnetic Separation of *Salmonella* From Foods and Their Detection Using Immunomagnetic Particle"; International Journal of Food Microbiology; 27 (1995); pp. 11-25.

Dickinson et al.; "New and Improved Strategies for the Rapid Detection and Differential Identification of Microbial Spores Using MALDI-TOFMS"; Proceedings of the 50th ASMS Conference on Mass Spectrometry and Allied Topics; Orlando, Florida; Jun. 2-6, 2002.

Dubow, Michael S.; "Bacterial Identification—Use of Phages"; Academic Press Encyclopedia of Virology; May 18, 2003.

Dziadkowiec et al.; "The detection of *Salmonella* in skimmed milk powder enrichments using conventional methods and immunomagnetic separation"; Letters in Applied Microbiology; 1995; pp. 361-364; vol. 20.

Favrin et al.; "Development and Optimization of a Novel Immunomagnetic Separation—Bacteriophage Assay for Detection of *Salmonella enterica* Serovar Enteritidis in Broth"; Applied and Environmental Microbiology; Jan. 2001; pp. 217-224; vol. 67, No. 1.

Gantt et al.; "Use of an Internal Control for Matrix-Assisted Laser Desorption/Ionization Time-of-Flight Mass Spectrometry Analysis of Bacteria"; J Am Soc Mass Spectrom; 1999; pp. 1131-1137; vol. 10.

Grant et al.; "Isolation of *Mycobacterium paratuberculosis* from Milk by Immunomagnetic Separation"; Applied and Environmental Microbiology; Sep. 1998; pp. 3153-3158; vol. 64, No. 9.

Hirsh et al.; "Rapid Detection of *Salmonella* spp. by Using Felix-O1 Bacteriophage and High-Performance Liquid Chromatography"; Applied and Environmental Microbiology, Jan. 1983, pp. 260-264.

Jenison et al.; "Silicon-based biosensors for rapid detection of protein or nucleic acid targets"; Clin. Chem; 2001; pp. 1894-1900; vol. 47, No. 10.

Jenison et al.; "Thin film biosensor for rapid detection of mecA from Methicillin-resistant *Staphylococcus aureus*"; Clin. Chem.; 2000; pp. 1501-1504; vol. 46, No. 9.

Kingsbury et al.; "Rapid Detection and Identification of Infectious Agents"; Academic Press, Inc.; New York; 1985.

Kodikara et al.; "Near on-line detection of enteric bacteria using lux recombinant bacteriophage"; FEMS Microbiology Letters; 1991; pp. 261-266; vol. 83.

Lynn et al.; "Identification of Enterobacteriaceae Bacteria by Direct Matrix-assisted Laser Desorption/Ionization Mass Spectrometric Analysis of Whole Cells"; Rapid Communication in Mass Spectrometry; Rapid Commun. Mass Spectrom.; 1999; pp. 2022-2027; vol. 13.

Madonna et al.; "Detection of bacteria from biological mixtures using immunomagnetic separation combined with matrix-assisted laser desorption/ionization time-of-flight mass spectrometry"; Raid Communication in Mass Spectrometry; Rapid Commun. Mass Spectrom.; 2001; pp. 1068-1074; vol. 15.

Madonna et al.; "Detection of *Escherichia coli* using immunomagnetic separation and bacteriophage amplification coupled with matrix-assisted laser desorption/ionization time-of-flight mass spectrometry"; Rapid Communications in Mass Spectrometry, 2003, vol. 17, pp. 257-263.

Madonna et al.; "Detection of *Esherichia coli* Using Immunomagnetic Separation and Bacteriophage Amplification Coupled With Matrix-Assisted Laser Desorption/Ionization Time-of-Flight Mass Spectrometry"; Wiley InterScience; DOI: 10.1002/rem.900; Dec. 24, 2002.

Mandeville et al., "Diagnostic and Therapeutic Applications of Lytic Phages", 2003 Anal. Lett., 36, 15, 3241-3259.

Pugh et al.; "A complete protocol using conductance for rapid detection of salmonellas in confectionery materials"; Letters in Applied Microbiology; 1988; pp. 23-27; vol. 7.

Pyle et al.; "Sensitive Detection of *Escherichia coli* O157:H7 in Food and Water by Immunomagnetic Separation and Solid-Phase Laser Cytometery"; Applied and Environmental Microbiology; May 1999; pp. 1966-1972.

Ryzhov et al.; "Characterization of the Protein Subset Desorbed by MALDI from Whole Bacterial Cells"; Analytical Chemistry; Feb. 15, 2001; pp. 746-750; vol. 73, No. 4.

Skjerve et al.; "Detection of *Listeria monocytogenes* in Foods by Immunomagnetic Separation"; Applied and Environmental Microbiology; Nov. 1990; pp. 3478-3481.

Stewart et al.; "The specific and sensitive detection of bacterial pathogens within 4 h using bacteriophage amplication"; Journal of Applied Microbiology, 1998, vol. 84, pp. 777-783.

Stewart, G.S.A.B.; "In vivo bioluminescence: new potentials for microbiology"; Letters in Applied Microbiology; 1990; pp. 1-8; vol. 10.

Strauss et al.; "Purification and Properties of Bacteriophage MS2 and of its Ribonucleic Acid"; J. Mol. Biol.; 1963; pp. 43-54; vol. 7.

Van De Plas et al.; "Colloidal Gold as a Marker in Molecular Biology: The Use of Ultra-Small Gold Particles"; Nonradioactive Labeling and Detection of Biomolecules; C. Kessler, Ed.; Spring-Verlag, NY; 1992; pp. 116-126.

Van Der Wolf et al.; "Immunomagnetic separation of *Erwinia carotovora* subsp. *atroseptica* from potato peel extracts to improve detection sensitivity on a crystal violet pectate medium or by PCR"; Journal of Applied Bacteriology; 1996; pp. 487-495; vol. 80.

Voorhees et al.; "A Rapid Determination of Bacterial Viability".

Wang et al.; "Investigation of Spectral Reproducibility in Direct Analysis of Bacteria Proteins by Matrix-assisted Laser Desorption/Ionization Time-of-flight Mass Spectrometry"; Rapid Communications In Mass Spectrometry; Rapid Commun. Mass Spectrom.; 1998; pp. 456-464; vol. 12.

Wyatt et al.; :Immunoassays for Food-poisoning Bacteria and Bacterial Toxins; James & James (Science Publishers) Ltd.and Chapman & Hall; London, Great Britain; 1992.

Yu et al.; "Immunomagnetic-Electrochemiluminescent Detection of *Escherichia coli* 0157 and *Salmonella typhimurium* in Foods and Environmental Water Samples"; Applied and Environmental Microbiology; Feb. 1996; pp. 587-592.

* cited by examiner

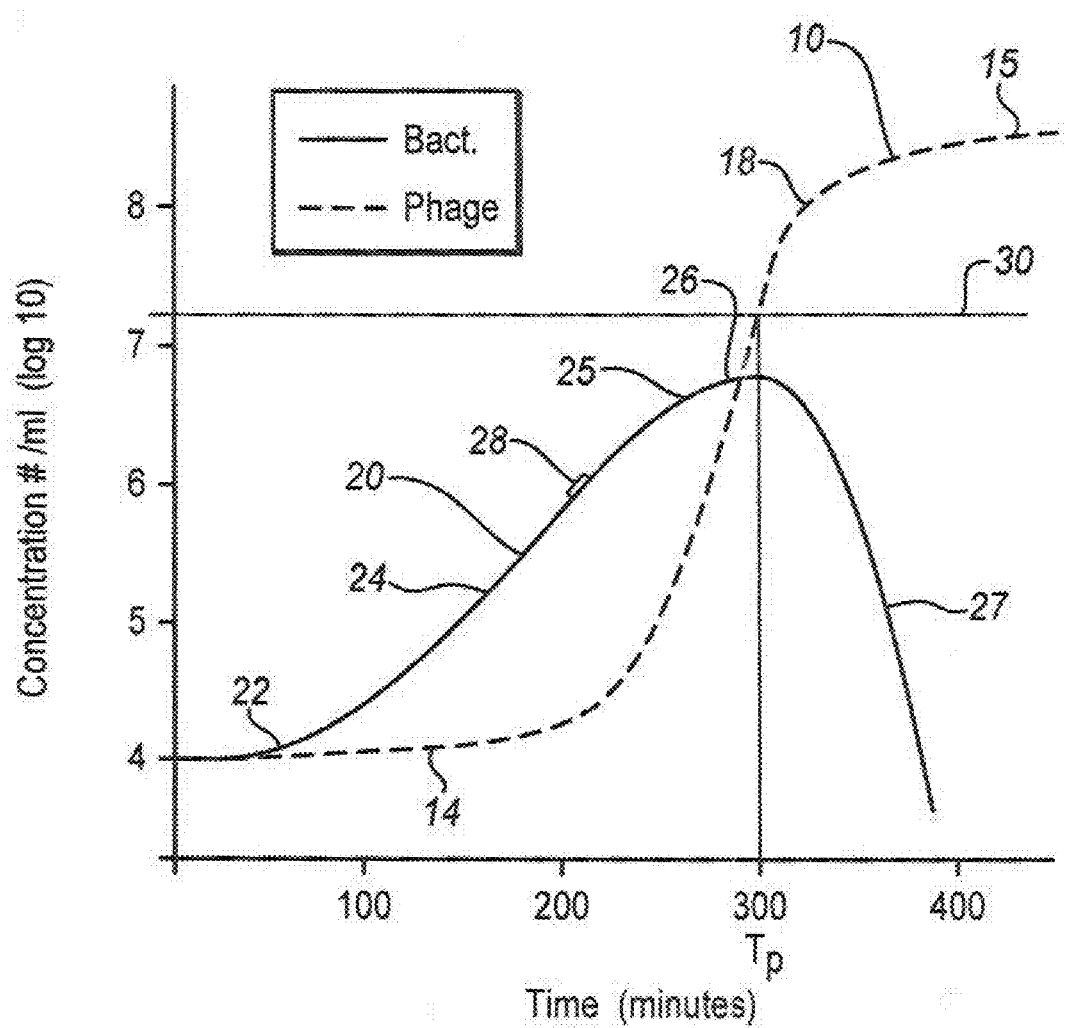

METHOD FOR ENHANCED SENSITIVITY IN BACTERIOPHAGE-BASED DIAGNOSTIC ASSAYS

CROSS-REFERENCE TO RELATED APPLICATIONS

This Application claims the benefit of U.S. Provisional Application No. 61/058,120 filed on Jun. 2, 2008. This application also is a Continuation-In-Part of U.S. patent application Ser. No. 12/346,656 filed Dec. 30, 2008; which is a divisional of U.S. patent application Ser. No. 10/823,294 filed Apr. 12, 2004; which claims the benefit of U.S. Provisional 60/544,437 filed Feb. 13, 2004, and 60/557,962 filed Mar. 31, 2004. All of the above patent applications, both provisional and non-provisional, are hereby incorporated by reference to the same extent as though fully contained herein.

FIELD OF THE INVENTION

The invention relates generally to the field of identification of microscopic living organisms, and more particularly to the identification of microorganisms using bacteriophage.

BACKGROUND OF THE INVENTION

Currently, bacteria that may be causing an infection or other health problem are identified by bacteria culture methods. Generally, it takes a day or several days to grow sufficient bacteria to enable the detection and identification of the bacteria. By that time, the person or persons infected by the bacteria may be very sick, or even dead. Thus, there is a need for more rapid detection and identification of bacteria. Further, when bacteria infection is suspected, a physician will often prescribe a broad spectrum antibiotic. This has led to the development of antibiotic resistant bacteria, which has further enhanced the need for more rapid detection of bacteria.

Bacteriophage-based methods have been suggested as a method to accelerate microorganism identification. Bacteriophage are viruses that have evolved in nature to use bacteria as a means of replicating themselves. A bacteriophage (or phage) does this by attaching itself to a bacterium and injecting its genetic material into that bacterium, inducing it to replicate the phage from tens to thousands of times. Some bacteriophage, called lytic bacteriophage, rupture the host bacterium releasing the progeny phage into the environment to seek out other bacteria. Thus, because of the sheer number of the bacteriophage after amplification, in principle it should be easier to detect the bacteriophage than to detect the bacteria. If, in addition the bacteriophage is specific to the bacteria, that is, if the bacteriophage amplification of a particular bacteriophage only occurs for specific bacteria, then the presence of amplified bacteria is then also an indication of the presence of the bacteria to which it is specific. Further, since the total incubation time for infection of a bacterium by parent phage, phage multiplication (amplification) in the bacterium to produce progeny phage, and release of the progeny phage after lysis can take as little as an hour depending on the phage, the bacterium, and the environmental conditions, in principle, bacteriophage amplification can result in much faster detection of bacteria. See, for example, U.S. Pat. No. 5,985,596 issued Nov. 16, 1999 and No. 6,461,833 B1 issued Oct. 8, both to Stuart Mark Wilson; and Angelo J. Madonna, Sheila VanCuyk and Kent J. Voorhees, "Detection Of *Escherichia Coli* Using Immunomagnetic Separation And Bacteriophage Amplification Coupled With Matrix-Assisted Laser Desorption/Ionization Time-Of-Flight Mass Spectrometry", Wiley InterScience, DOI:10.1002/rem.900, 24 Dec. 2002, which references are hereby incorporated by reference to the same extent as though fully disclosed herein.

In each of the methods of the above references, samples potentially containing target bacteria are incubated with bacteriophage, as specific as possible for those bacteria. In the presence of the bacteria, the bacteriophage infect the bacteria and replicate in the bacteria resulting in the production of a measurable signal indicating the presence of the target bacteria. Some methods utilize the detection of progeny phage released from infected target bacteria as a means of detection and identification. In this case, progeny phage are not produced if the parent phage do not successfully infect the target bacteria. The degree to which the phage will infect the bacteria if the phage and bacteria are in the same sample is called the infectious sensitivity of the phage. Still other methods rely on the detection of phage replication products rather than whole progeny phage. For example, luciferase reporter bacteriophage produce luciferase when they successfully infect target bacteria. The luciferase then produces light that, if detected, indicates the presence of target bacteria in the sample. The promise of these methods has lead to much research on bacteriophage-based identification of microorganisms. However, as of this writing, no commercially successful method of bacteriophage-based identification has been developed.

In any method based on phage amplification, it is necessary to separate the signal that arises from the parent bacteriophage from the signal from the progeny bacteriophage. U.S. Pat. No. 5,498,525 issued Mar. 12, 1996 to Rees et al. solves this problem by destroying, removing, neutralizing, or inactivating the parent bacteriophage; and U.S. Pat. No. 7,166,425 issued Jan. 23, 2007 to Madonna et al. solves this problem by using a quantity of parent bacteriophage that is below the detection limit of the detection technology. However, to be sure that a lower level of bacteria are detected, the quantity of bacteriophage is kept as high as possible while still being under the detection limit.

While, in principle, bacteriophage-based identification of bacteria should work, commercial success of a bacteriophage-based assay has been impeded by practical problems. In practice, available bacteriophage are not selective to a single strain of bacteria or are not adequately sensitive to the bacterial strain it is desired to detect. Moreover, in the real world, any sample of bacteriophage will contain not only the bacteriophage that are selective of the target bacteria, but other bacteriophage that are selective of non-target bacteria. As a result, in practice, the bacteriophage-based bacteria detection process does not produce a large enough signal in a short enough time to be competitive with bacteria culture methods. We shall refer to this as "assay sensitivity" to differentiate it from infectious sensitivity. Clearly, it would be highly desirable if a bacteriophage process could be provided that had increased selectivity, increased infectious sensitivity, and/or increased test sensitivity and still retained the fast detection of bacteria that is the promise of bacteriophage amplification methods, the potential of which has been driving research in this field.

BRIEF SUMMARY OF THE INVENTION

The invention solves the above problems, as well as other problems of the prior art, by reducing the number of parent bacteriophage as compared to the prior art. Surprisingly, reducing the number of parent bacteriophage increases both the sensitivity of the test and the selectivity of the bacteriophage. By reducing the number of parent bacteriophage thought to be optimum in the prior art, for the first time a commercially competitive process for detecting bacteria using bacteriophage becomes available.

The invention provides a method of determining the presence or absence of a target microorganism in a sample to be tested, the method comprising: (a) combining with the sample an amount of bacteriophage capable of attaching to the target microorganism to create a bacteriophage exposed sample, the amount of bacteriophage being between $1\times10^6$ pfu/mL and $7\times10^6$ pfu/mL; (b) providing conditions to the bacteriophage-exposed sample sufficient to allow the bacteriophage to attach to the target microorganism; and (c) assaying the bacteriophage-exposed sample to detect the presence or absence of a bacteriophage marker to determine the presence or absence of the target microorganism. Preferably, the microorganism is a bacterium, and the assaying comprises detecting the bacteriophage marker as an indication of the presence of the target bacterium in the sample. Preferably, the providing comprises providing conditions to permit the bacteriophage to infect the target microorganism and to multiply in the target microorganism. Preferably, the amount of the bacteriophage is between $2\times10^6$ pfu/mL and $6\times10^6$ pfu/mL. Preferably, the amount of the bacteriophage is between $2.5\times10^6$ pfu/mL and $4\times10^6$ pfu/mL.

In another aspect, the invention provides a method of determining the presence or absence of a target microorganism in a sample to be tested, the method comprising: (a) combining with the sample an amount of bacteriophage capable of attaching to the target microorganism to create a bacteriophage-exposed sample; (b) providing conditions to the bacteriophage-exposed sample sufficient to allow the bacteriophage to attach to the target microorganism; and (c) assaying the bacteriophage-exposed sample to detect the presence or absence of a bacteriophage marker to determine the presence or absence of the target microorganism; wherein the amount of the bacteriophage is between 10% to 70% of the threshold number of bacteriophage that the assay can detect. Preferably, the amount of the bacteriophage is between 20% and 50% of the threshold. Preferably, the amount of the bacteriophage is about a third of the threshold.

The invention solves the problem of providing high test sensitivity and high selectivity in short times, generally in four hours or less. Numerous other features, objects, and advantages of the invention will become apparent from the following description when read in conjunction with the accompanying drawing.

BRIEF DESCRIPTION OF THE DRAWING

FIG. 1 is a graph of bacteriophage concentration versus time and bacteria concentration versus time in a sample that has an initial bacteria concentration of $10^4$ bacteria per milliliter and an initial bacteriophage concentration of approximately $10^4$ lytic phage.

DETAILED DESCRIPTION OF THE INVENTION

In this disclosure, the terms "bacteriophage" and "phage" include bacteriophage, phage, mycobacteriophage (such as for TB and paraTB), mycophage (such as for fungi), mycoplasma phage or mycoplasmal phage, and any other term that refers to a virus that can invade living bacteria, fungi, mycoplasmas, protozoa, yeasts, and other microscopic living organisms and uses them to replicate itself. Here, "microscopic" means that the largest dimension is one millimeter or less. Bacteriophage are viruses that have evolved in nature to use bacteria as a means of replicating themselves. A phage does this by attaching itself to a bacterium and injecting its DNA (or RNA) into that bacterium, and inducing it to replicate the phage hundreds or even thousands of times. This is referred to as phage amplification.

Whether the bacteriophage has infected the bacteria is determined by an assay that can identify the presence of a bacteriophage or bacterial marker. In this disclosure, a bacteriophage marker is any biological or organic element that can be associated with the presence of a bacteriophage. Without limitation, this may be the bacteriophage itself, a lipid incorporated into the phage structure, a protein associated with the bacteriophage, RNA or DNA associated with the bacteriophage, or any portion of any of the foregoing. In this disclosure, a bacterial marker is any biological or organic element that is released when a bacterium is lysed by a bacteriophage, including cell wall components, bacterial nucleic acids, proteins, enzymes, small molecules, or any portion of the foregoing. Preferably, the assay not only can identify the bacteriophage marker, but also the quantity or concentration of the bacteriophage or bacterial marker. In this disclosure, determining the quantity of a microorganism is equivalent to determining the concentration of the microorganism, since if you have one, you have the other, since the volume of the sample is nearly always known, and, if not known, can be determined. Determining the quantity or concentration of something can mean determining the number, the number per unit volume, determining a range wherein the number or number per unit volume lies, or determining that the number or concentration is below or above a certain critical threshold. Generally, in this art, the amount of a microorganism is given as a factor of ten, for example, $2.3\times10^7$ bacteria per milliliter (ml).

Some bacteriophage, called lytic bacteriophage, rupture the host bacterium, releasing the progeny phage into the environment to seek out other bacteria. The total reaction time for phage infection of a bacterium, phage multiplication, or amplification in the bacterium, through lysing of the bacterium takes anywhere from tens of minutes to hours, depending on the phage and bacterium in question and the environmental conditions. Once the bacterium is lysed, progeny phage are released into the environment along with all the contents of the bacteria. The progeny phage will infect other bacteria that are present, and repeat the cycle to create more phage and more bacterial debris. In this manner, the number of phage will increase exponentially until there are essentially no more bacteria to infect. The concept underlying the art of using bacteriophage to detect bacteria is that the huge numbers of phage that are created during phage amplification can be detected more easily than the much smaller number of bacteria; thus, phage amplification can be used to detect the presence of bacteria.

A fundamental principle that allows particular bacteria to be detected via bacteriophage amplification followed by an assay of a bacteriophage marker is that a particular bacteriophage will infect only a particular bacterium. That is, the bacteriophage is specific to the bacteria. Thus, if a particular bacteriophage that is specific to particular bacteria is introduced into a sample, and later the bacteriophage has been found to have multiplied, the bacteria to which the bacteriophage is specific must have been present in the sample. In this way, the prior art teaches that bacteriophage amplification can be used to identify specific bacteria present in a sample.

However, bacteriophage that are 100% specific to a single bacteria species that it is desired to detect are not present in nature. Further, bacteriophage found in nature also are not 100% sensitive to the bacteria that it is desired to detect. That is, they do not always succeed in infecting the target bacteria. In the prior art, it was believed that it was important to provide as large of a bacteriophage amplification signal as possible, and that the way to do this was to add as much bacteriophage as possible to the sample. Even in the case of U.S. Pat. No. 7,166,425, in which the number of bacteriophage added was kept below the detection limit of a MALDI detection process, still as much bacteriophage was added as possible while still being below the detection limit.

The inventors have found that the selectivity and sensitivity of a bacteriophage selection process can be increased by decreasing the quantity of bacteriophage added to a sample. This surprising result can be understood by considering FIG. 1.

FIG. 1 is a logarithmic graph 10 of phage concentration versus time for a test sample initially containing $10^4$ target bacteria for which the phage were specific. The FIGURE also includes a graph 20 showing the concentration of the target bacteria versus time for the same test sample. At time zero, approximately $10^4$ lytic phage were added to the sample. The sample was then incubated. At first, the phage do not even appreciably amplify, since the probability that the phage and bacteria interact is very small at these starting concentrations. Essentially, the infection process cannot occur until there are enough bacteria present in the sample for the phage to find them. Thus, the phage line remains flat at 14. However, the incubation also grows the bacteria. After about forty minutes, the number of bacteria begins to increase as shown at 22 and accelerates in region 24. The point at which bacteriophage begin to rapidly find and infect the host bacteria occurs at a quite narrow bacterial concentration range 28 owing to diffusion and binding effects. In the example of FIG. 1, this occurs at a bacterial concentration of about $10^5$ to $10^6$ bacteria per ml. The number of bacteriophage does not increase immediately, because it takes some time for the bacteriophage to multiply after infecting the bacteria. The bacteriophage rise becomes exponential at about 240 minutes, which causes the bacterial growth to decelerate in the region 25 and then turn around at 26. After the bacteria concentration peaks, the phage curve flattens to create a knee 18 at about 330 minutes and peaks at about 360 minutes. The number of bacteria steeply decreases in the region 27 as the phage infect and kill the bacteria and the phage number continues to increase. By 360 minutes, the phage versus time curve is essentially flat since all but a minor portion of the bacteria are dead. No permissive bacterial hosts of said phage are added to the sample.

The prior art was of the view that by using a larger number of parent phage the curve 14 would rise to a higher plateau 15, and this seems reasonable. However, the height of the plateau 15 is relatively insensitive to the amount of parent phage added. The larger the number of phage, the faster they multiply, true, but this is only at first. A larger number ends up killing the bacteria faster causing a quick decline in the number of bacteria and a resulting quick plateauing of the phage curve.

To understand how the sensitivity can be improved by reducing the number of bacteriophage, note that the bacteriophage rapidly kill the bacteria when their numbers get sufficiently high. If the number of bacteriophage is, for example, $3 \times 10^7$ pfu/mL, the bacteriophage will kill the bacteria before the amplification process can go very far, and a false negative will be produced because the signal-to-noise ratio of the test will be too small. Currently, the threshold level of bacteriophage that can be detected is about $1 \times 10^7$ pfu/mL. Even at this level, and some distance below it, the bacteriophage will kill the bacteria too quickly. At about $6 \times 10^6$ pfu/mL, a good signal-to-noise ratio is obtained. A better signal-to-noise ratio is obtained at $3 \times 10^6$ pfu/mL.

As discussed above, samples of bacteriophage will always include a fair number of non-desired bacteriophage that are selective to a different bacteria than the target bacteria, i.e., a non-target bacteria. If the non-target bacteria are present, the non-desired bacteriophage will multiply and produce an erroneous positive test. To understand how the selectivity of the bacteriophage can be improved by reducing the number of bacteriophage, it should first be recognized that the bacteriophage curve 14 will be lower for non-desired strains of phage because the number of these bacteriophage will be lower than the desired strain. If the number of parent phage added to the sample is kept far enough below the threshold of bacteriophage detection, then the number of the undesirable strain bacteriophage will be so low that a signal will not be produced. That is, the number of bacteriophage produced by the undesired strains by the bacteriophage amplification process will stay below the detection threshold.

As described in PCT Application No. PCT/US07/085268 filed Nov. 20, 2007, which is incorporated herein by reference, bacteriophage can be used to detect bacteria simply using the property that phage attach to the bacteria, that is, without the amplification step. For example, first, labeled phage are added to a sample potentially containing target bacteria. Second, the sample is incubated for a predetermined period of time that is at least sufficiently long for the phage to bind to the target bacteria if present. Third, the sample is added to a detector or a well containing phage attached to a substrate. When the labeled phage-target bacteria complex binds to the bound phage, the sandwich is completed. If the phage is labeled with colored beads, a visible signal is produced, as in a lateral flow strip. If the phage is labeled with an enzyme, as in an ELISA assay, the well is rinsed, enzyme substrate is added, and a detectable signal is subsequently produced. The phage capture assay can also be run in many other ways to produce many different types of signals familiar to those skilled in the art. If the phage capture assay result is a positive, it indicates the presence of the target bacteria in the sample.

The bacteria detection processes using bacteriophage can be configured to determine antibiotic susceptibility of the target bacteria; and the invention is also applicable to such an antibiotic susceptibility test. For example, a sample potentially containing target bacteria is divided into two parts: Sample One and Sample Two. A phage amplification process or phage capture assay process described previously are performed on Sample One to ascertain the presence of the target bacteria in the sample. Samples One and Two are tested simultaneously or serially beginning with Sample One. If the presence of the target bacteria is already known via some other method, then Sample One is not needed nor is the associated phage assay. Sample Two is treated differently. Initially, the concentration of the target bacteria in Sample Two preferably should be below the detection limit of the phage assay. If it might be above the limit, then an optional first process comprising diluting Sample Two to reduce the concentration to below the detection limit preferably is done. An antibiotic is added to Sample Two at a specific concentration. Then, Sample Two is optionally incubated for a predetermined period of time to allow the antibiotic to act upon the target bacteria. A reagent containing phage that is specific to the target bacteria is added to Sample Two; and Sample Two is incubated for a predetermined time. The previously described phage amplification assay process or phage capture binding assay detection process is performed. If the target bacteria is resistant to the antibiotic, it will grow and reach a concentration that is detected in the assay producing a positive result. The positive result indicates that the target bacterium is present in the assay; and the particular strain is resistant to the tested antibiotic. If the target bacterium is susceptible to the tested antibiotic, it will not grow in Sample Two; and the assay result will be negative. This result combined with a positive result on the assay performed on Sample One with no antibiotic will indicate that the target bacteria is present and that it is susceptible to the antibiotic.

Again, in the antibiotic susceptibility test, if the concentration of parent bacteriophage is too high, the bacteria may be prematurely killed; and a false positive for susceptibility or false negative for resistance may result.

The inventors have found that, for a commercially useful bacteria detection process, the number of parent phage added to the sample should be in a range from 10% to 70% of the threshold number of bacteriophage that the pertinent assay can detect. More preferably, the number of parent phage should be in a range between 20% and 50% of the threshold, and most preferably should be about a third of the threshold. Preferably, the number of parent bacteriophage should be between $1\times10^6$ pfu/mL and $7\times10^6$ pfu/mL, and more preferably between $2\times10^6$ pfu/mL and $6\times10^6$ pfu/mL, and most preferably between $2.5\times10^6$ pfu/mL and $4\times10^6$ pfu/mL.

Many other phage-based methods and apparatus used to identify the microorganism and/or to determine the antibiotic resistance test or antibiotic susceptibility can be enhanced by the method and apparatus of the invention. For example, a phage amplification process, such as a process described in US Patent Application Publication No. 2005/0003346 entitled "Apparatus And Method For Detecting Microscopic Living Organisms Using Bacteriophage" may be enhanced by the present invention. A process of attaching to a microorganism, such as described in PCT Patent Application Ser. No. PCT/US06/12371 entitled "Apparatus And Method For Detecting Microorganisms Using Flagged Bacteriophage" may also be enhanced. Any other phage-based identification process may also be used.

There has been described an improvement to the conventional bacteria detection methods using bacteriophage that, for the first time, leads to a commercially useful process because the sensitivity and selectivity of the detection method become comparable to the selectivity and sensitivity of conventional bacteria culture detection processes. It should be understood that the particular embodiments shown in the drawing and described within this specification are for purposes of example and should not be construed to limit the invention, which will be described in the claims below. Further, it is evident that those skilled in the art may now make numerous uses and modifications of the specific embodiment described, without departing from the inventive concepts. Equivalent structures and processes may be substituted for the various structures and processes described; the subprocesses of the inventive method may, in some instances, be performed in a different order; or a variety of different materials and elements may be used. Consequently, the invention is to be construed as embracing each and every novel feature and novel combination of features present in and/or possessed by the microorganism detection apparatus and methods described.

What is claimed as new and desired to be protected by Letters Patent of the United States is:

1. A method of determining the presence or absence of a target microorganism in a sample to be tested, said method comprising:
    (a) providing a sample in which the presence or absence of said target microorganism is not known;
    (b) combining with said sample an amount of bacteriophage capable of attaching to said target microorganism to create a bacteriophage exposed sample, said amount of bacteriophage being between $1\times10^6$ pfu/mL and $7\times10^6$ pfu/mL;
    (c) providing conditions to said bacteriophage-exposed sample sufficient to allow said bacteriophage to attach to said target microorganism, to infect said target microorganism, and to multiply in said target microorganism; and
    (d) assaying said bacteriophage-exposed sample to detect the presence or absence of a bacteriophage marker to determine the presence or absence of said target microorganism.

2. A method as in claim 1 wherein said microorganism is a bacterium and said assaying comprises detecting said bacteriophage marker as an indication of the presence of said target bacterium in said sample.

3. A method as in claim 1 wherein said amount of said bacteriophage is between $2\times10^6$ pfu/mL and $6\times10^6$ pfu/mL.

4. A method as in claim 1 wherein said amount of said bacteriophage is between $2.5\times10^6$ pfu/mL and $4\times10^6$ pfu/mL.

5. A method as in claim 1 wherein a known permissive bacterial host of the said phage is not added to said sample.

6. A method of determining the presence or absence of a target microorganism in a sample to be tested, said method comprising:
    (a) providing a sample in which the presence or absence of said target microorganism is not known;
    (b) combining with said sample an amount of bacteriophage capable of attaching to said target microorganism to create a bacteriophage-exposed sample;
    (c) providing conditions to said bacteriophage-exposed sample sufficient to allow said bacteriophage to attach to said target microorganism, to infect said target microorganism, and to multiply in said target microorganism; and
    (d) assaying said bacteriophage-exposed sample to detect the presence or absence of a bacteriophage marker to determine the presence or absence of said target microorganism;
    wherein said amount of said bacteriophage is between 10% to 70% of the threshold number of bacteriophage that said assay can detect.

7. A method as in claim 6 wherein said amount of said bacteriophage is between 20% and 50% of said threshold.

8. A method as in claim 6 wherein said amount of said bacteriophage is about a third of said threshold.

9. A method as in claim 6 wherein a known permissive bacterial host of the said phage is not added to said sample.

* * * * *